(12) United States Patent  (10) Patent No.: US 7,952,772 B2
Sanders  (45) Date of Patent: May 31, 2011

(54) PHOTONIC CRYSTAL FIBER SENSOR

(75) Inventor: Glen A. Sanders, Scottsdale, AZ (US)

(73) Assignee: Honeywell International Inc., Morristown, NJ (US)

( * ) Notice: Subject to any disclaimer, the term of this patent is extended or adjusted under 35 U.S.C. 154(b) by 259 days.

(21) Appl. No.: 12/463,009

(22) Filed: May 8, 2009

(65) Prior Publication Data
US 2010/0284020 A1 Nov. 11, 2010

(51) Int. Cl.
G01B 9/02 (2006.01)
G02B 6/00 (2006.01)

(52) U.S. Cl. ......... 358/480; 356/73.1; 385/12; 385/123; 385/125; 250/227.18

(58) Field of Classification Search ................. 356/436, 356/71–73, 73.1, 480; 385/12, 123–127, 385/115, 39; 250/227.18, 227.13
See application file for complete search history.

(56) References Cited

U.S. PATENT DOCUMENTS

| 4,834,496 | A | 5/1989 | Blyler, Jr. et al. |
| 5,009,505 | A | 4/1991 | Malvern |
| 5,315,673 | A | 5/1994 | Stetter et al. |
| 5,802,236 | A | 9/1998 | DiGiovanni et al. |
| 6,205,263 | B1 | 3/2001 | Lieberman et al. |
| 6,243,522 | B1 | 6/2001 | Allan et al. |
| 6,334,017 | B1 | 12/2001 | West |
| 6,334,019 | B1 | 12/2001 | Birks et al. |
| 6,496,632 | B2 * | 12/2002 | Borrelli et al. ........ 385/123 |
| 6,879,386 | B2 * | 4/2005 | Shurgalin et al. ....... 356/73.1 |
| 7,327,460 | B2 | 2/2008 | Sanders et al. |
| 7,336,859 | B2 | 2/2008 | Sanders |
| 7,372,574 | B2 | 5/2008 | Sanders et al. |
| 7,388,671 | B2 | 6/2008 | Sanders et al. |
| 7,446,880 | B2 * | 11/2008 | Vollmer et al. ........ 356/480 |
| 7,671,325 | B2 * | 3/2010 | Sanders et al. ........ 250/227.18 |
| 7,805,028 | B2 * | 9/2010 | Li et al. ........... 385/12 |

(Continued)

FOREIGN PATENT DOCUMENTS

EP 1213583 A1 12/2002

(Continued)

OTHER PUBLICATIONS

Cordeiro et al., "Lateral Access to the Holes of Photonic Crystal Fibers—Selective Filling and Sensing Applications", "Optics Express", Sep. 4, 2006, pp. 8403-8412, vol. 14, No. 18, Publisher: Optical Society of America.

(Continued)

Primary Examiner — Sang Nguyen
(74) Attorney, Agent, or Firm — Fogg & Powers LLC

(57) ABSTRACT

Apparatus and method for chemical and biological agent sensing. An example sensing apparatus includes a resonator having a resonance frequency. The resonator includes a coil of a photonic crystal fiber. The photonic crystal fiber has a solid region configured to guide a substantially single optical mode of light having, a cladding surrounding an exterior of the solid region, and at least one hollow core within the cladding. The cladding contains at least one hollow core. The photonic crystal fiber is configured to introduce a fluid that may contain an analyte to the hollow core. The photonic crystal fiber is configured so that the light interacts with the fluid. The resonator is configured to produce a resonance signal centered at the resonance frequency. A predetermined change in the resonance signal indicates a presence of a quantity of the analyte in the fluid.

12 Claims, 6 Drawing Sheets

U.S. PATENT DOCUMENTS

| | | | |
|---|---|---|---|
| 7,809,225 B2 * | 10/2010 | Bouma et al. | 385/123 |
| 2003/0109055 A1 | 6/2003 | Lehmann et al. | |
| 2006/0188398 A1 * | 8/2006 | Yano et al. | 422/82.01 |
| 2006/0227331 A1 | 10/2006 | Vollmer et al. | |
| 2007/0201030 A1 | 8/2007 | Sanders | |
| 2007/0230859 A1 * | 10/2007 | Bock et al. | 385/12 |
| 2007/0242275 A1 | 10/2007 | Spartz et al. | |
| 2008/0079947 A1 | 4/2008 | Sanders et al. | |
| 2008/0116361 A1 | 5/2008 | Sanders et al. | |
| 2008/0137091 A1 | 6/2008 | Sanders et al. | |
| 2008/0203281 A1 | 8/2008 | Sanders et al. | |
| 2008/0212104 A1 | 9/2008 | Sanders | |

FOREIGN PATENT DOCUMENTS

| | | |
|---|---|---|
| EP | 1923693 A1 | 5/2008 |
| EP | 2000795 | 12/2008 |
| EP | 2020712 A1 | 2/2009 |

OTHER PUBLICATIONS

European Patent Office, "European Search Report", Sep. 6, 2010, Published in: EP.

Huang et al., "Fabrication of Functional Microstructured Optical Fibers Through a Selective-Filling Technique", "Applied Physics Letters", Nov. 29, 2004, vol. 85, No. 22, Publisher: American Institute of Physics.

Konorov et al., "Photonic-Crystal Fiber as a Multifunctional Optical Sensor and Sample Collector", "Optics Express", May 2, 2005, pp. 3454-3459, vol. 13, No. 9, Publisher: Optical Society of America.

Seraji et al., "Design of Micro Loop Ring Resonator Tunable Filter Based on PCF", Dec. 8, 2008, Publisher: IEEE.

Sumetsky et al., "Optical Liquid Ring Resonator Sensor", "Optical Society of America", Oct. 29, 2007, vol. 15, No. 22, Publisher: Optics Express.

White et al., "Liquid-Core Optical Ring-Resonator Sensors", "2006 Optical Society of America", May 1, 2006, pp. 1319-1321, vol. 31, No. 9, Publisher: Optics Letters, Published in: Washington DC.

Grigoriy Emiliyanov et al., Multi-Antibody Biosensing with Topas Microstructured Polymer Optical Fiber, 19th International Conference on Optical Fibre Sensors, Edited by David Sampson, Stephen Collins, Kyunghwan Oh, Ryozo Yamauchi, Proc. of SPIE vol. 7004, 70043A, (2008), pp. 70043A-1 through 70043A-4.

Soan Kim et al., A Dual-Concentric-Core Photonic Crystal Fiber for Broadband Dispersion Compensation, Journal of the Korean Physical Society, vol. 49, No. 4, Oct. 2006, pp. 1434 through 1437.

* cited by examiner

PHOTONIC CRYSTAL FIBER SENSOR

BACKGROUND OF THE INVENTION

The presence of a chemical or biological substance has traditionally been detected by utilizing one or more chemical reactions. These chemical reactions are usually irreversible, i.e. the reactions are not reset if the chemical or biological substance is removed from the device. Detection devices that utilize irreversible chemical reactions are typically time consuming and/or expensive to maintain because at least a portion of the detection device needs to be replaced or steps need to be undertaken to reset the device if a quantity of the chemical or biological substance has been detected.

Alternatively, a detection device may be reversible, i.e. the device can be reset automatically if a detected chemical or biological substance is removed. Thus, a reversible device is usually reusable. One type of reversible detection device uses a physics-based, spectroscopic solution to determine the presence of a substance without a chemical reaction. Specifically, light is passed through a waveguide. The light extends into the environment and is reactive to at least one contaminant particle in an adjacent environment. A detector is used to determine the specific contaminant particle and its concentration in the environment based the characteristics of the received light.

An example reversible device uses ultra-thin nanowire fibers as waveguides. The nanowire fiber is thin enough to allow a portion of a lightwave to propagate in, and thereby interact with, the environment adjacent to the nanowire. However, the use of nanowire fiber is limited because nanowire is typically very fragile. It is also difficult to form nanowire coils having orientations other than a straight path due, in part, to the nanowire manufacturing process. These limitations influence the type of platform capable of housing a device and the structures that can be utilized. These limitations are compounded in a chemical or biological sensing device because the nanowire fiber needs to be exposed to the surrounding environment in order to interact with the substance to be detected. In such a platform, it is difficult to ensure only light and substance interactions, without interference from its packaging environment since it needs to be supported. Thus, the supporting environment severely compromises the measurement. Moreover, it is desirable to increase the length of the nanowire fiber used in a sensor because increasing pathlength increases measurement sensitivity. However, increasing the length of the nanowire leads to a device that is even more fragile.

SUMMARY OF THE INVENTION

The present invention includes devices and methods for determining a presence of an analyte. A sensor includes a light source, a detector, a resonator, and a processor. The light source produces light that is transferred to the resonator. At least a portion of the light propagating in the resonator is transferred to the detector. The resonator includes a photonic crystal fiber including a coil section. The photonic crystal fiber includes a solid region configured to guide a substantially single optical mode of light passing through a cladding. The cladding region includes at least one hollow region. The cladding region is configured so that the at least one hollow region may receive a fluid that may contain a quantity of an analyte. The solid region, the light, and the cladding are configured so that the light extends into the at least one hollow region. The light passes through resonator multiple times. The detector detects the resonance signal indicative of the light traveling in the resonator. The processor determines whether a measurable quantity of the analyte is present in the fluid based on the resonance signal detected by the detector. The processor may also identify the analyte based on the resonance signal or identify the quantity of the analyte present in the fluid.

In accordance with further aspects of the invention, the resonator includes an input and an output configured to pass the fluid through the at least one hollow region configured to receive the fluid. The input and the output may pass the fluid through the at least one hollow region by applying a pressure differential to the input and output.

In accordance with other aspects of the invention, the resonator includes a plurality of holes extending from an exterior of the photonic crystal fiber into the at least one hollow region configured to receive the fluid.

In accordance with still further aspects of the invention, a method for sensing an analyte includes passing a fluid that may contain a quantity of an analyte through at least a portion of at least one hollow channel of a photonic crystal fiber coil, propagating a light wave through a resonator so that at least a portion of the light wave extends into the at least one hollow region containing the fluid, determining whether the fluid contains the quantity of the analyte based on a detected resonance signal.

In accordance with yet other aspects of the invention, the method determines the concentration of the analyte in the fluid based on the detected resonance signal.

As will be readily appreciated from the foregoing summary, the invention provides devices and methods for determining the presence of an analyte.

BRIEF DESCRIPTION OF THE DRAWINGS

Preferred and alternative embodiments of the present invention are described in detail below with reference to the following drawings:

FIG. 2-1 is a cross-sectional view of a photonic crystal fiber with hollow channels used in the device shown in FIG. 1;

FIG. 2-2 is a perspective, x-ray view of a photonic crystal fiber with hollow channels including a plurality of holes formed in accordance with an embodiment of the present invention;

FIG. 3-1 is a mode field distribution useful in understanding the photonic crystal fiber shown in FIGS. 1 and 2;

FIG. 3-2 is a distribution showing the loss of light per pass through the resonator shown in FIG. 1;

FIG. 4-1 is a graphical representation of the resonator output when an analyte is not present in detectable quantities in the hollow channel or channels of the fiber;

FIG. 4-2 is a graphical representation of the resonator output with when a significant amount of the analyte is present in the hollow channels or channels of the fiber.

DETAILED DESCRIPTION OF THE INVENTION

An apparatus and method are provided for sensing one or more chemical or biological substances. Applicant hereby incorporates U.S. Pat. No. 7,336,859 and Published U.S. Patent Applications 2008/0212104 and 2008/0116361 in their entireties by reference.

Figure 1:
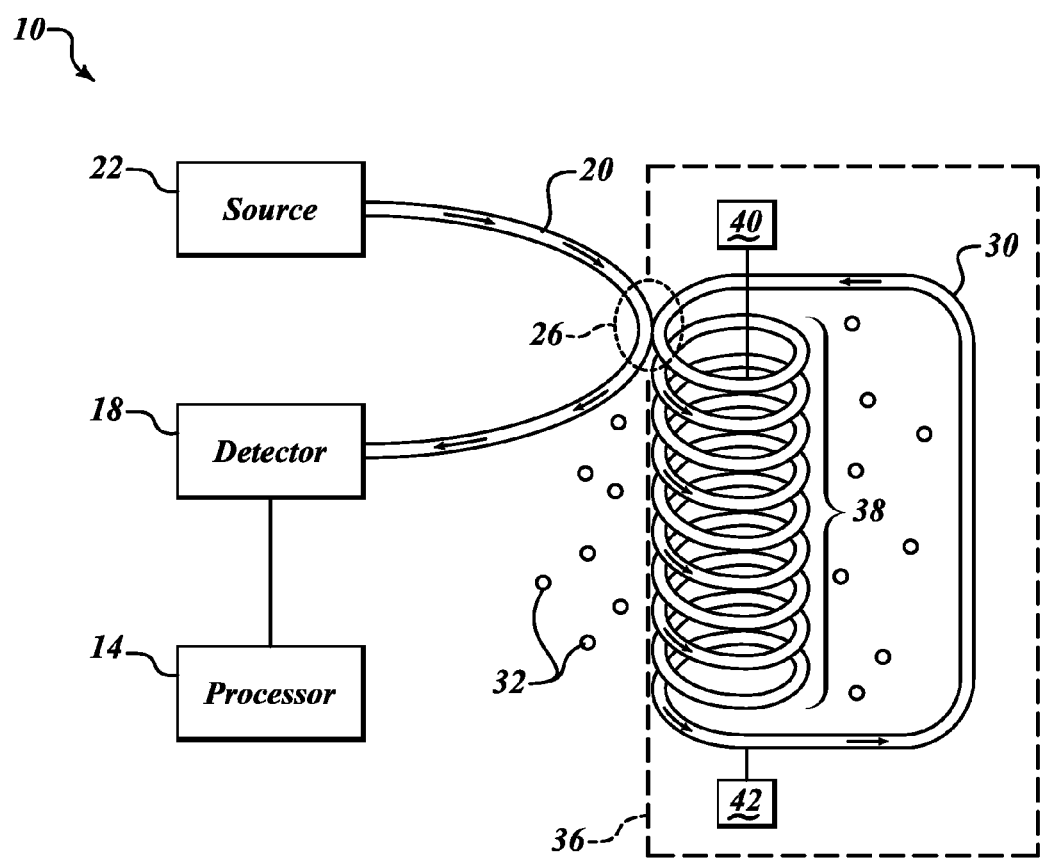
FIG. 1 is a schematic diagram of an analyte sensing device formed in accordance with an embodiment of the present invention.

FIG. 1 shows an analyte sensor 10. As used herein, "analyte" means a specific chemical or biological substance sought to be detected. The analyte sensor 10 includes a detector 18, a light source 22, a first fiber 20, and a resonator 36. The light source 22 and the detector 18 are in optical communication via the first fiber 20. The first fiber 20 is also in optical communication with the resonator 36. An optical connection between the first fiber 20 and the resonator 36 is defined by a coupling junction 26.

The light source 22 includes a tunable monochromatic light source such as, but not limited to, a laser diode. In one embodiment, the light source 22 scans frequencies over a period of time. Accordingly, the frequency of a resulting light wave may be a single value at any single point in time, but the frequency can be adjusted up or down according to the frequency desired for sensing.

The resonator 36 includes a second fiber 30 that forms a coil 38. The second fiber 30 has two ends that are optically connected to form a closed light path by conventional methods such as utilizing a mechanical splice, fusion bonding, or free space optics. Alternatively, any optical element that reintroduces a substantial portion of light emerging from one end of the second fiber 30 to the other end of the second fiber 30 may be used to optically connect the two ends. Light introduced into the second fiber 30 propagates there through multiple times.

Figures 1, 2:
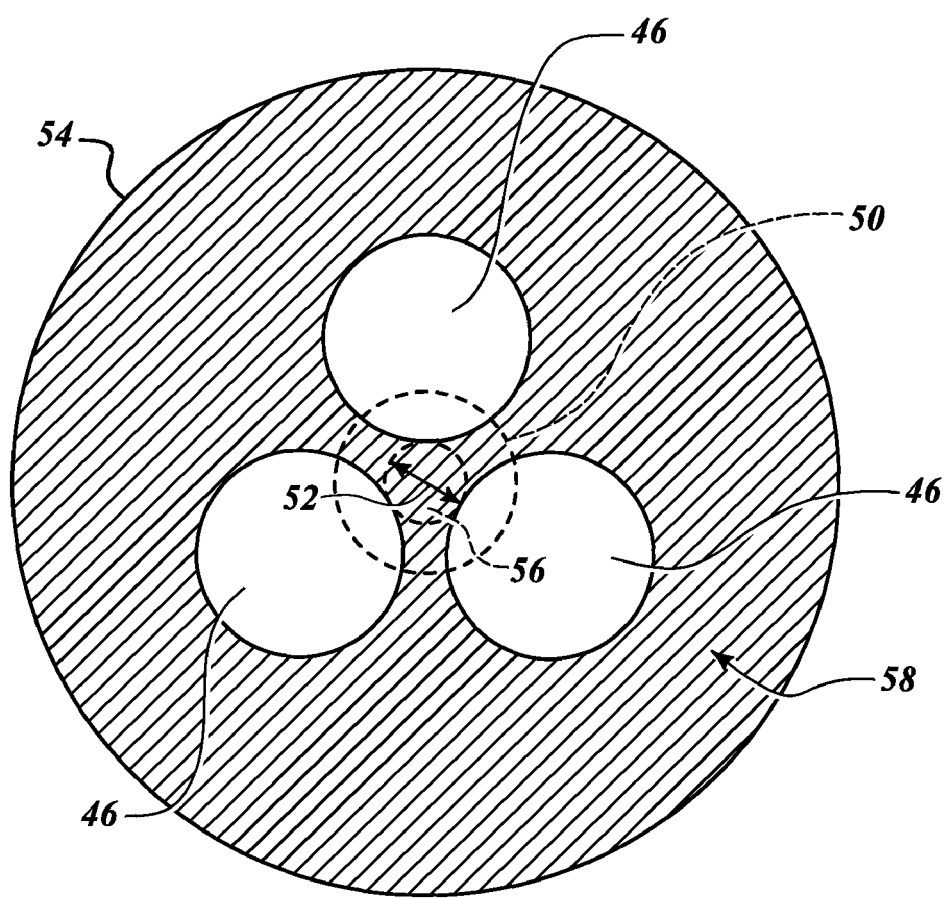
Figure 2:
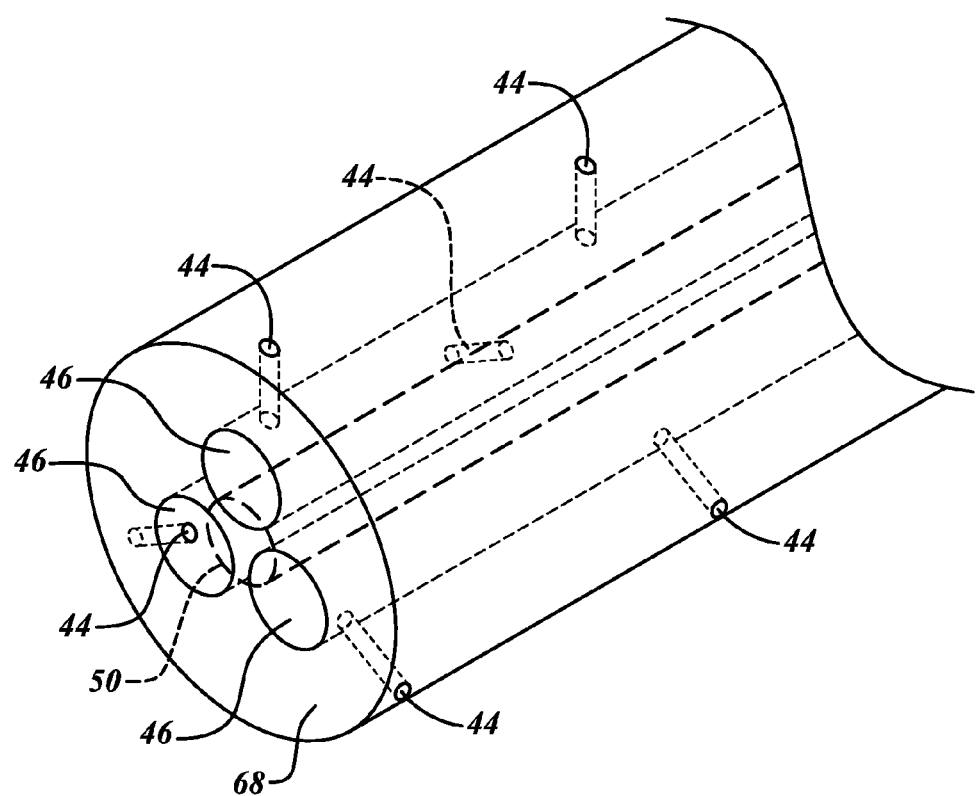

The second fiber 30 includes a single mode photonic crystal fiber (PCF) with one or more hollow channels. FIG. 2 illustrates a cross-sectional view of one embodiment of a PCF 54 included in the second fiber 30. PCF is known in the art. See, for example, U.S. Pat. No. 5,802,236 to DiGiovanni et al.; U.S. Pat. No. 6,243,522 to Allen et al.; U.S. Pat. No. 6,334,017 to West et al.; and U.S. Pat. No. 6,334,019 to Birks et al., all of which are hereby incorporated herein by reference in their entireties.

The PCF 54 includes a cladding region 58, three round-cross-section hollow channels 46, and solid region 56 where an optical field 50 can be guided. The solid region 56 and the hollow channels 46 reside within the cladding region 58. Each hollow channel 46 is a free space hole. The hollow channels 46 have a refractive index that is lower than the refractive index of the solid region 56. The cladding 58 is composed of a glass material that is usually the same material as in the solid region 56. The hollow channels 46 do not intersect each other. The hollow channels 46 are positioned so that a solid region 56 between the hollow channels 46 forms an index of refraction cross-sectional profile that allows light in the optical field 50 to be guided with a fraction of light in the solid region 56 and a fraction of light guided in hollow channels 46.

In one embodiment, a diameter 52 of the solid region 56 is smaller than a wavelength of light emitted from the light source 22. As will be discussed in more detail herein, light propagates in the optical field 50, and at least a portion of the light intensity passes through the hollow channels 46. The amount of light intensity to be extended into the cladding region 58 and/or hollow channels 46 may be varied based on a variety of factors (e.g. refractive index of cladding region, thickness of cladding region, or number and size of hollow channels). It is understood that the PCF 54 could be formed with various geometries and having various compositions and could include various quantities and configurations of hollow regions 46 and cladding region 58.

In one embodiment, the resonator 36 is formed with a PCF having an extremely low bend loss so that the coil section 38 of the resonator 36 has a relatively large number of turns about a substantially small area. Bend loss refers to a quantity of light that exits a fiber at a turn. In one embodiment, the coil section 38 has approximately 20-40 turns about a one centimeter diameter. More or less turns can be utilized depending on a variety of factors of the analyte sensor 10 such as package size, cost, and signal-to-noise ratio. In comparison to prior art devices made from nanowires, the resonator 36 allows for both an increased effective pathlength and a smaller package. Increasing the effective pathlength is desirable because it allows for increased device sensitivity (i.e. greater signal-to-noise ratio) as well as increased robustness.

Light transfers between the first fiber 20 and the second fiber 30 at the coupling junction 26. It is understood by those skilled in the art that light may be transferred between the first fiber 20 and the second fiber 30 by a variety of techniques and configurations to provide the intended function of coupling light into the resonator 36 and/or coupling light to the first fiber 20 from the resonator 36 (i.e. the second fiber 30).

Light transfers between the first fiber 20 and the second fiber 30 occurs, in part, because the core regions of the two fibers are brought into close proximity, often with the cladding region 58 thinned down or polished off. In one embodiment, the first fiber 20 and second fiber 30 are positioned adjacent to each other to facilitate light transfers from fiber to fiber. Alternatively, the cladding of first fiber 20 and second fiber 30 may be shaved, thinned, or polished by conventional techniques thereby allowing the inner portions of fibers 20 and 30 to be attached to each other. As an example, attaching may be accomplished with optical contact or epoxy.

The percentage of the light transferring between the first fiber 20 and the second fiber 30 at the coupling junction 26 depends on multiple factors such as, but not limited to, the speed of light traveling in the fibers 20 and 30, the distance between the optical fields in first fiber 20 and the second fiber 30, the size and configuration of the hollow channels 46, and the composition of the cladding region 58.

FIG. 2-2 shows an embodiment of the second fiber 30 where the second fiber 30 includes a plurality of holes 44 extending from an exterior of the PCF 54 through at least a portion of a cladding region 68 and into the hollow cores 46. In one embodiment the plurality of holes 44 terminate at the hollow channels 46, i.e. the holes 44 do not extend into the hollow channels 46. The plurality of holes 44 can be formed using conventional laser drilling/boring techniques. The holes 44 expose the hollow channels 46 to an adjacent environment. In operation, the fluid that might contain the analyte 32 diffuses or otherwise permeates into the hollow channels 46 via the plurality of holes 44 from the adjacent environment. As used herein "fluid" means matter in a substantially gaseous phase, matter in a substantially liquid phase, or matter in a state of equilibrium between the gaseous and liquid phases.

In another embodiment, the hollow channels 46 of the second fiber 30 are configured to include an input 40 and an output 42 (FIG. 1). The input 40 and the output 42 define one or more pathways passing through the cladding region 58 in/out of the hollow channel 46. The holes 44 are the input 40 and the output 42. A fluid that may contain an analyte 32 is introduced into the hollow channel 46 at the input 40. As an example, the fluid could be a sample of an adjacent environment or it could be a sample from a different environment. A pressure differential is applied to the input 40 and the output 42 using conventional methods. The pressure differential "sucks" the fluid into and/or through the hollow channels 46. In one embodiment, the input 40 and the output 42 can be configured to introduce the fluid to just one or some, but not all, of the hollow channels 46.

In operation, light from the source 22 propagates through the resonator 36 multiple times in one direction. The frequency of the light from the source 22 is adjusted or scanned so that it propagates at a resonance frequency. The wavelength of light from the source 22 is adjusted to pass through a region of interest where the analyte 32 has a particular change in optical properties or an expected absorption response. A resonance signal is produced from the light traveling in the region of the resonance frequency. A portion of the light propagating through the resonator 36 is passed from the second fiber 30 to the first fiber 20 at the coupling junction 26. The resonance signal corresponding to the light passing through the resonator 36 is detected by the detector 18. The detector 18 is typically a semiconductor photodiode, such as those made from silicon or InGaAsP, depending on wavelength of light used.

Analyte sensing is accomplished by introducing the fluid that may contain the analyte 32 into the hollow channels 46. If the analyte 32 is not present in the fluid, a first resonance signal is detected by the detector 18. If the analyte 32 is present in the fluid, the analyte 32 interacts (e.g. absorbs) with a portion of the light propagating within the fiber 30. The interaction between the light and the analyte 32 produces a second resonance signal, i.e. it alters the first resonance signal at a given wavelength. In other words, the specific resonance signal produced by the resonator 36 depends on the presence of the analyte 32 in the hollow channels 46.

A processor 14 determines the presence and/or quantity of the analyte 32 in the fluid based on the signal detected by the detector 18. In one embodiment, the processor 14 is configured to determine the concentration of the analyte 32 in the fluid based on the signal detected by the detector 18.

Figures 1, 3:
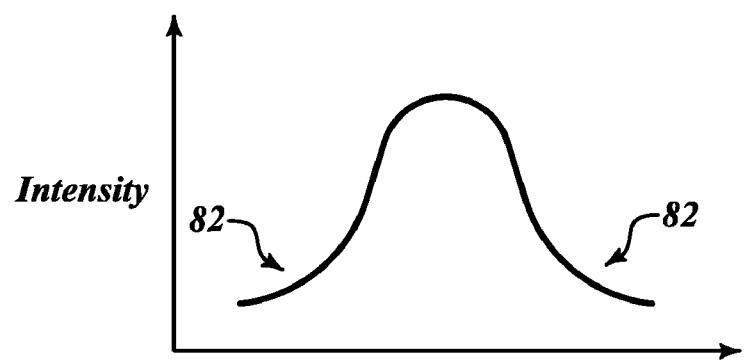
Figures 2, 3:
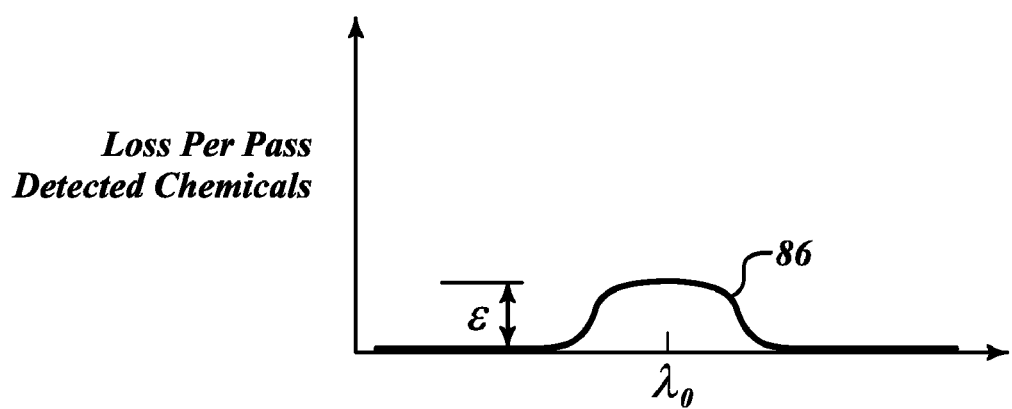

FIG. 3-1 is an example mode field distribution useful in understanding the PCF 54 shown in FIGS. 1 and 2. Specifically, the mode field distribution of the light emitted from the source 22 has an optical energy spatial distribution that is generally Gaussian shaped with evanescent tails 82. A significant quantity of the light intensity extends into the hollow channels 46 because the size of the solid region 56 (FIG. 2-1) in between the hollow channels 46 in which the optical field 50 is resident is small relative to the wavelength of the light emitted from the source 22.

FIG. 3-2 shows a graph representative of a loss per pass 86 (denoted as ϵ) associated with the presence of a quantity of an analyte in the second fiber 30. The loss per pass 86 represents the light energy absorbed by the analyte for each pass through the resonator 36. Loss per pass 86 is proportional to the concentration of the analyte.

Figures 1, 4:
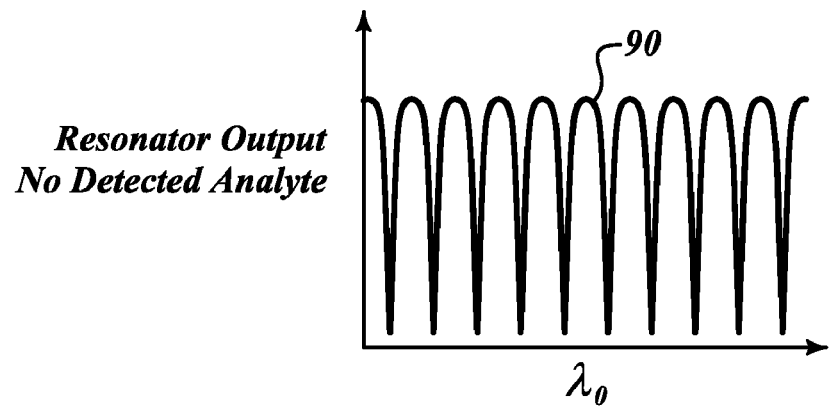
Figures 2, 4:
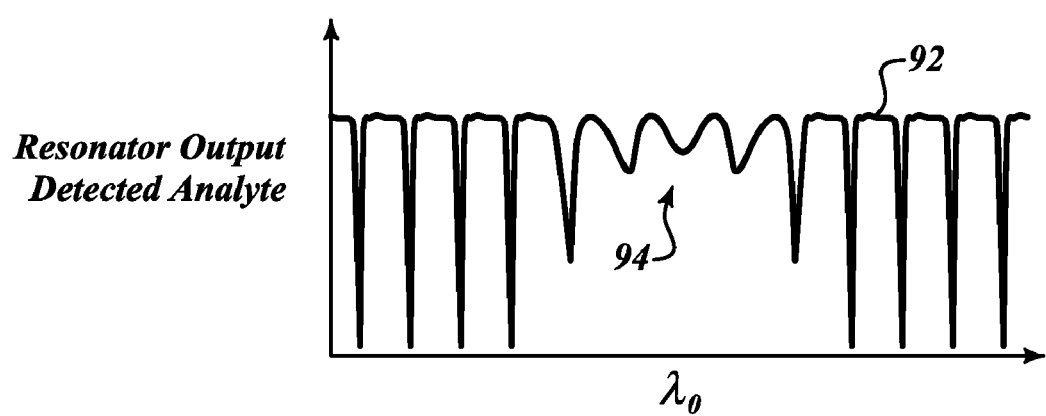

FIG. 4-1 shows a first resonance lineshape 90 determined by the processor 14 based on the signal detected by the detector 18. The first resonance lineshape 90 includes a narrow profile. The first resonance lineshape 90 indicates that essentially no light energy was absorbed in the resonator 36, i.e. no significant loss. Accordingly, the first resonance lineshape 90 indicates that a detectable or measurable quantity of the analyte 32 is not present in the hollow channels 46.

FIG. 4-2 shows a second resonance scan with a first narrow lineshape 92 at one frequency in the scan determined by the processor 14 based on the resonance signal detected by the detector 18. A second lineshape 94 in the scan includes a broadened lineshape with a shallower dip. The second lineshape 94 indicate that some light energy has been absorbed while passing through the resonator 36. Thus, the change in the second resonance lineshape from 92 to 94 indicates the presence of a quantity of the analyte 32 in the hollow channels 46. The processor 14 may determine the specific quantity of the chemical present in the fluid based on a signal corresponding to the lineshapes 92 and 94.

Figure 5:
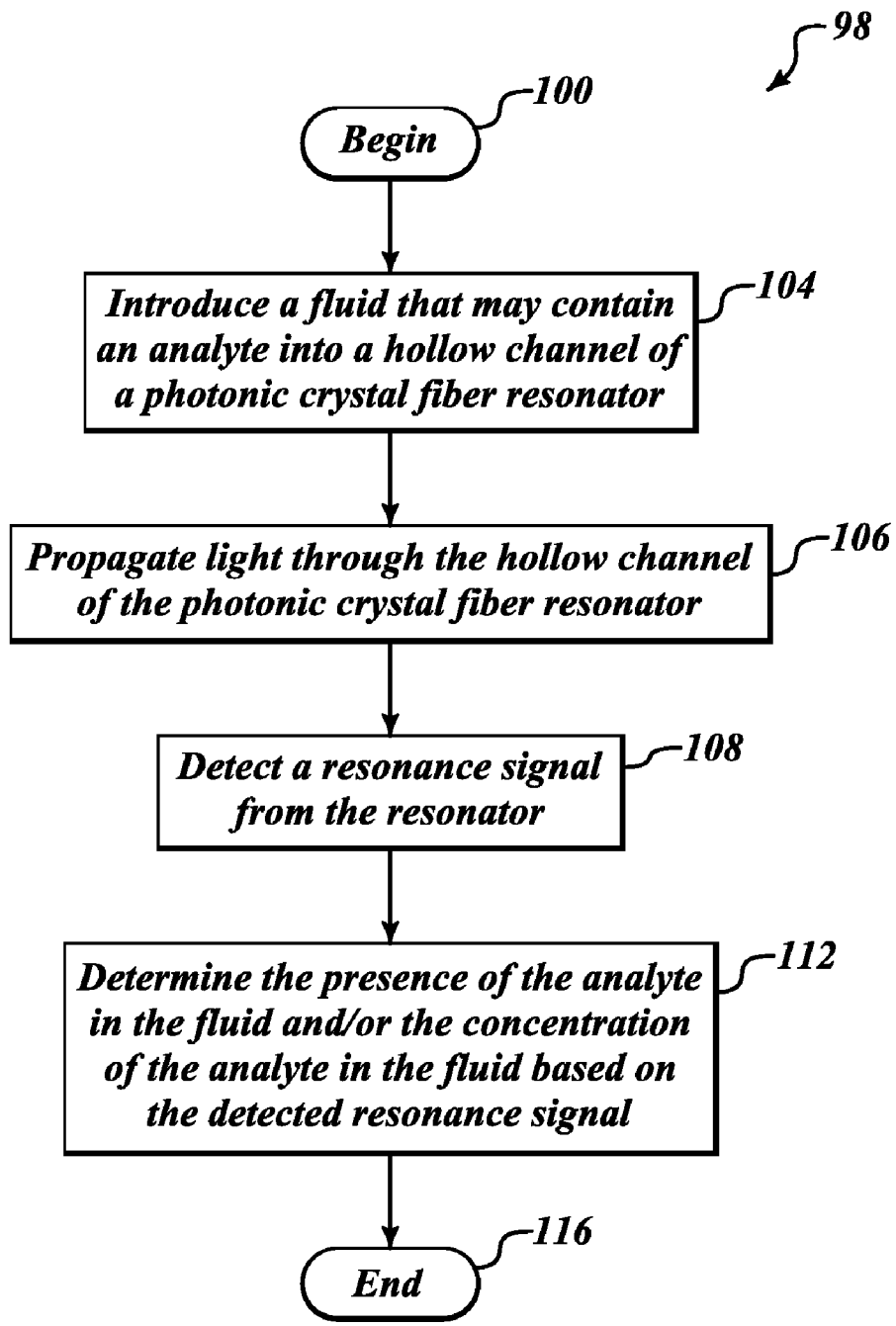
FIG. 5 is a flow diagram of a method for sensing an analyte in accordance with the present invention.

FIG. 5 is a flow diagram of a process 98 for sensing one or more chemical/biological agents in an environment. The process begins at block 100. At block 104, a fluid that may include the analyte 32 is passed through the second fiber 30. As discussed in more detail above, the fluid is passed through the hollow channels 46 by diffusing in from an adjacent environment through the plurality of holes 44 extending from the exterior of the PCF 54 into the hollow channels 46. Alternatively, the fluid is introduced or passed through the hollow channels 46 via the input 40 and output 42 by a pressure differential applied to the input 40 and the output 42. At block 106, light from the light source 22 is propagated through the resonator 36. The light source 22 is scanned through a wavelength or wavelength region of interest where the analyte 32 has a molecular absorption resonance line or is known to exhibit certain properties. In one embodiment, the light is scanned over a broad region of wavelengths. At block 108 a resonance signal is detected by the detector 18 based on the light propagating through the resonator 36. At block 112, the processor 14 determines the quantity (if any) of the analyte 32 present based on the detected resonance signal. In one embodiment, the processor 14 identifies the specific chemical or biological substance present in the fluid based on the resonance signal. In another embodiment, the processor 14 determines the concentration of the analyte 32 in the fluid based in part on the resonance signal. At block 116, the process 98 ends.

The process 98 may be reinitiated without any adjustment to the fiber 30 even if a quantity of the analyte 32 was previously determined to be present in the fluid. In other words, the process 98 is reversible.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A photonic crystal fiber resonator comprising:
    a solid region; and
    a cladding surrounding an exterior of the solid region, the cladding comprising at least one hollow channel configured to receive a fluid from an external source, the fluid may contain a quantity of an analyte,
    wherein the photonic crystal fiber has a coil section having at least one turn, the photonic crystal fiber has two ends configured to be in optical communication with each other, the solid region is configured to guide a substantially single optical mode of light that extends into the at least one hollow channel containing the fluid, the photonic crystal fiber resonator is configured to pass the substantially single optical mode of light through the at least one hollow channel containing the fluid multiple times, the photonic crystal fiber resonator is configured to resonate a first resonance signal when the substantially single optical mode of light is frequency-scanned through a region about a resonance frequency if a measurable quantity of the analyte absent from the fluid and resonate a second resonance signal other than the first resonance signal when the substantially single optical mode of light is frequency-scanned through the region about the resonance frequency if the measurable quantity of the analyte is present in the fluid.

2. The photonic crystal fiber resonator of claim 1, wherein the coil section has about 20 to about 40 turns.

3. The photonic crystal fiber resonator of claim 1, wherein the coil encircles an area having a diameter of about 1 cm.

4. The photonic crystal fiber resonator of claim 1, wherein the cladding comprises three hollow channels.

5. The photonic crystal fiber resonator of claim 1, wherein the cladding has a refractive index greater than the refractive index of both the hollow channels and the fluid, and wherein a position of the hollow channels is selected to extend a portion of an evanescent tail of the substantially single optical mode of light into the at least one hollow channel.

6. The photonic crystal fiber resonator of claim 1, wherein the photonic crystal fiber further comprises an input and an output, the input and the output are configured to pass the fluid that may contain the analyte through a substantial portion of the at least one hollow channel.

7. The photonic crystal fiber of claim 6, wherein the input and the output are configured to apply a pressure differential to the at least one hollow core in order to pass the fluid there through.

8. The photonic crystal fiber resonator of claim 1, wherein the photonic crystal fiber further comprises a plurality of holes extending from an exterior of the photonic crystal fiber into the at least one hollow channel, the plurality of holes configured to pass the fluid that may contain a measurable quantity of the analyte through a substantial portion of the at least one hollow channel.

9. A sensor for sensing an analyte, the sensor comprising:
a tunable light source configured to provide a substantially single optical mode of light;
a detector;
a processor; and
a resonator configured to resonate light of a predefined frequency, the resonator comprising a coil, the coil comprising a photonic crystal fiber, the photonic crystal fiber comprising:
a solid region configured to guide a substantially single optical mode of light, the substantially single optical mode of light passing through the coil multiple times; and
a cladding surrounding an exterior of the solid region, the cladding comprising at least one hollow channel configured to receive a fluid from an external source, the fluid may contain more than a measurable quantity of an analyte, a portion of the single optical mode of light extends into the at least one hollow channel configured to receive a fluid,
wherein the tunable light source is in optical communication with the detector and the resonator, the resonator is in optical communication with the detector, and the detector is in one of electrical or optical communication with the processor, and wherein the detector detects a resonance signal centered at the resonance frequency as the tunable light source is tuned through a region about the resonance frequency, a predetermined change in the resonance signal detected by the detector indicates the quantity of the analyte in the fluid.

10. The sensor of claim 9, wherein the photonic crystal fiber further comprises an input and an output, the input and the output configured to pass the fluid that may contain the analyte through a substantial portion of the at least one hollow channel.

11. The photonic crystal fiber of claim 10, wherein the input and the output are configured to apply a pressure differential to the at least one hollow channel.

12. The sensor of claim 9, wherein the photonic crystal fiber further comprises a plurality of holes extending from an exterior of the photonic crystal fiber into the at least one hollow channel, the plurality of holes configured to pass the fluid that may contain the analyte of interest through a substantial portion of the at least one hollow channel.

* * * * *